United States Patent [19]

Kondo et al.

[11] 4,349,618

[45] Sep. 14, 1982

[54] PHOTOCONDUCTIVE COMPOSITIONS AND ELECTROPHOTOGRAPHIC LIGHT-SENSITIVE MATERIALS USING SAID COMPOSITIONS

[75] Inventors: Syunichi Kondo; Hirotsugu Nomaguchi; Hideo Sato, all of Asaka, Japan

[73] Assignee: Fuji Photo Film Co., Ltd., Kanagawa, Japan

[21] Appl. No.: 287,849

[22] Filed: Jul. 29, 1981

[30] Foreign Application Priority Data

Jul. 29, 1980 [JP] Japan .............................. 55/104209

[51] Int. Cl.$^3$ .............................................. G03G 7/00
[52] U.S. Cl. .................................................. 430/83; 430/81
[58] Field of Search ................................... 430/81, 83

[56] References Cited

U.S. PATENT DOCUMENTS

| | | | |
|---|---|---|---|
| 3,037,861 | 6/1962 | Hoegl et al. | 430/81 X |
| 3,384,488 | 5/1968 | Tulagin et al. | 430/32 |
| 3,384,565 | 5/1968 | Tulagin et al. | 430/32 |
| 3,484,237 | 12/1969 | Shattuck et al. | 430/81 X |
| 3,510,419 | 5/1970 | Carreira et al. | 430/34 |

*Primary Examiner*—James R. Hoffman
*Attorney, Agent, or Firm*—Sughrue, Mion, Zinn, Macpeak & Seas

[57] ABSTRACT

A photoconductive composition comprising a photoconductive substance and a thiobarbituric acid derivative, and an electrophotographic light-sensitive material comprising a support having a layer of the photoconductive composition thereon.

14 Claims, No Drawings

PHOTOCONDUCTIVE COMPOSITIONS AND ELECTROPHOTOGRAPHIC LIGHT-SENSITIVE MATERIALS USING SAID COMPOSITIONS

FIELD OF THE INVENTION

This invention relates to a photoconductive composition and a high sensitive electrophotographic light-sensitive medium prepared using the photoconductive composition.

BACKGROUND OF THE INVENTION

Utilization of organic light-semiconductors in electrophotography has heretofore been studied. From German Patent Publication No. 1,068,115 and U.S. Pat. No. 3,037,861, it is known that polyvinyl carbazole is photoconductive and can be used in electrophotographic processes. Furthermore, the German Patent Publication discloses that addition of a small amount of dye increases the photosensitivity of polyvinyl carbazole.

German Patent Publication No. 1,572,347 and U.S. Pat. No. 3,484,237 disclose an electrophotographic recording medium bearing a photoconductive coating film prepared from a photoconductive composition comprising a polymer of a heterocyclic vinyl compound, e.g., polyvinyl carbazole and 0.49 to 1.23 mols of 2,4,7-trinitro-9-fluorenone per mol of the repeating unit of the polymer.

The electrophotographic recording medium as disclosed in German Unexamined Patent Publication (OLS) No. 1,797,561 has an electrophotographic coating film prepared from a photoconductive composition containing equal parts by weight of 2,4,7-trinitro-9-fluorenone and polyvinyl carbazole.

R. M. Schefelt describes in *IBM Journal of Research and Development*, Vol. 15, No. 1, pages 75 to 89 (1971) that the above-described recording media have excellent properties resulting from charge transfer complexes constituting their photoconductive coating films. Furthermore, the disclosure is that a number of substances which are described as sensitizers for polyvinyl carbazole have low mutual-solubility with polyvinyl carbazole and when used in higher concentrations, these substances adversely influence the photosensitivity (ibid., p. 76) and that none of these substances are as useful as 2,4,7-trinitro-9-fluorenone (ibid., p. 77).

Trinitrofluorenone is a relatively expensive substance and has very high physiological activity.

SUMMARY OF THE INVENTION

An object of this invention is to provide compounds which, when used in combination with photoconductive substances, exhibit a photosensitivity equal to that of the conventional polyvinyl carbazole-trinitrofluorenone composition and which are available industrially and at low cost.

It has now been found that the object of this invention is attained by using thiobarbituric acid derivatives.

This invention, therefore, provides in one embodiment, a photoconductive composition comprising a photoconductive substance and a thiobarbituric acid derivative represented by formula (1) or (2) below:

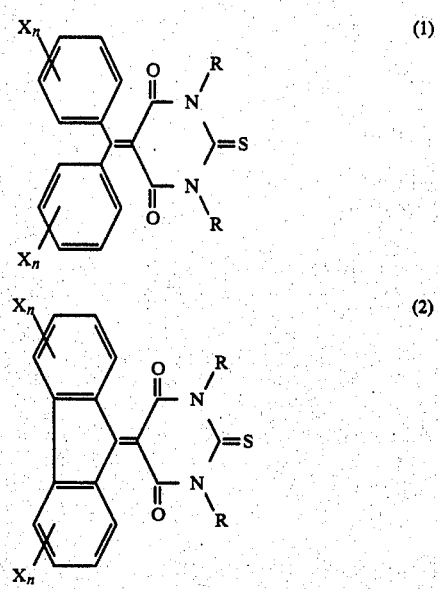

wherein X represents a hydrogen atom or a substituent having a Hammett's meta-position substituent constant ($\sigma m$) value of at least +0.2, n represents 1 or 2, and R represents an alkyl group containing 1 to 12 carbon atoms or a phenyl group.

This invention further provides, in a second embodiment, an electrophotographic light-sensitive material comprising a support having an electrically conductive surface and a photoconductive composition layer described above provided on the support.

DETAILED DESCRIPTION OF THE INVENTION

The Hammett's meta-position substituent constant ($\sigma m$) value used in this invention means $\sigma$ value at the meta-position defined in Hammett's Law and the values are disclosed in the Japanese version of J. E. Leffler, "Rates and Equilibria of Organic Reactions", which is translated by Yûho Tsuno and titled *Yûki Hanno Sokudo Ron* (Hirokawa Shoten, Tokyo (1968)).

Examples of substituents having a Hammett $\sigma m$ value of at least 0.2 include a cyano group, an acetyl group, a methoxycarbonyl group, an ethoxycarbonyl group, a carboxyl group, a nitro group, a —PO$_3$H group, a mercapto group, a methoxythiocarbonyl group, a methylsulfinyl group, a methylsulfonyl group, a sulfamoyl group, a fluorine atom, a chlorine atom, a bromine atom, an iodine atom, an iodyl group, and 2-nitrovinyl group.

The thiobarbituric acid derivatives which can be used in the photoconductive composition of this invention are represented by formula (1) or (2) below:

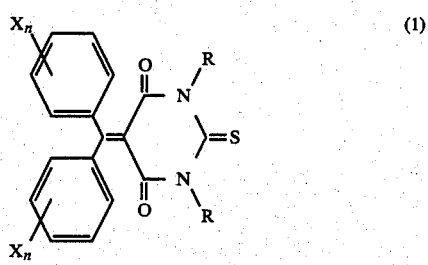

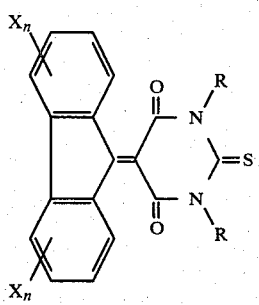

(2)

wherein X represents a hydrogen atom or a substituent having a Hammett's meta-position substituent constant ($\sigma$m) value of at least +0.2, n represents 1 or 2, and R represents an alkyl group containing 1 to 12 carbon atoms or a phenyl group.

In formula (1), X may be positioned at any of the carbon atoms of the benzene nucleus linked to the carbon atom of the methylene group, and preferably it is at the p- or o-position. In formula (2), X may be at any position of the fluorenone ring, and preferably it is at the 2-, 3-, 4-, 5-, 6- or 7-position. In formulas (1) and (2), all X may be the same or different.

The alkyl group containing 1 to 12 carbon atoms, represented by R may be either straight or branched. In addition, the alkyl group may have one or more of substituent of a hydroxyl group, an alkoxyl group containing 1 to 5 carbon atoms or a halogen atom such as chlorine, bromine, etc. Examples of such alkyl groups include a methyl group, an ethyl group, a propyl group, a butyl group, a pentyl group, a hexyl group, a heptyl group, an octyl group, a nonyl group, a decyl group, a dodecyl group, an isopropyl group, an isobutyl group, an isoamyl group, an isohexyl group, a sec-butyl group, a neopentyl group, a tert-butyl group and a tert-pentyl group. Of these groups, a methyl group, an ethyl group, a propyl group, a butyl group and an iso-propyl group are preferred.

A phenyl group represented by R may include a substituted phenyl group having one or more of substituent of a hydroxyl group, an alkyl group containing 1 to 5 carbon atoms, an alkoxyl group containing 1 to 5 carbon atoms or a halogen atom such as chlorine, bromine, etc.

Thiobarbituric acid derivatives represented by formula (1) are 5-diphenylmethylenethiobarbituric acid (or 5-($\alpha$-phenylbenzylidene)thiobarbituric acid) derivatives. Typical examples of these derivatives are given below:

5-Diphenylmethylene-1,3-dimethylthiobarbituric acid
5-Diphenylmethylene-1,3-diethylthiobarbituric acid
5-Diphenylmethylene-1,3-propylthiobarbituric acid
5-Diphenylmethylene-1,3-isopropylthiobarbituric acid
5-Diphenylmethylene-1,3-butylthiobarbituric acid
5-Diphenylmethylene-1,3-diphenylthiobarbituric acid
5-($\alpha$-Phenyl-p-chlorobenzylidene)-1,3-dimethylthiobarbituric acid
5-($\alpha$-Phenyl-p-chlorobenzylidene)-1,3-diethylthiobarbituric acid
5-($\alpha$-Phenyl-p-chlorobenzylidene)-1,3-diphenylthiobarbituric acid
5-($\alpha$-Phenyl-p-bromobenzylidene)-1,3-dimethylthiobarbituric acid
5-($\alpha$-Phenyl-p-bromobenzylidene)-1,3-diethylthiobarbituric acid
5-($\alpha$-Phenyl-p-bromobenzylidene)-1,3-diphenylthiobarbituric acid
5-($\alpha$-Phenyl-p-cyanobenzylidene)-1,3-dimethylthiobarbituric acid
5-($\alpha$-Phenyl-p-cyanobenzylidene)-1,3-diethylthiobarbituric acid
5-($\alpha$-Phenyl-p-cyanobenzylidene)-1,3-diphenylthiobarbituric acid
5-($\alpha$-Phenyl-p-nitrobenzylidene)-1,3-dimethylthiobarbituric acid
5-($\alpha$-Phenyl-p-nitrobenzylidene)-1,3-diethylthiobarbituric acid
5-($\alpha$-Phenyl-p-nitrobenzylidene)-1,3-diphenylthiobarbituric acid
5-bis(p-Chlorophenyl)methylene-1,3-diethylthiobarbituric acid
5-bis(p-Cyanophenyl)methylene-1,3-diethylthiobarbituric acid
5-bis(p-Nitrophenyl)methylene-1,3-diethylthiobarbituric acid
5-($\alpha$-o-Chlorophenyl-p-nitrobenzylidene)-1,3-diethylthiobarbituric acid
5-($\alpha$-o-Nitrophenyl-p-nitrobenzylidene)-1,3-diethylthiobarbituric acid Thiobarbituric acid derivatives represented by formula (2) are 5-(9-fluorenylidene)thiobarbituric acid derivatives. Typical examples of these derivatives are given below:

5-(9-Fluorenylidene)-1,3-diethylthiobarbituric acid
5-(2,4-Dinitro-9-fluorenylidene)-1,3-diethylthiobarbituric acid
5-(2,4,7-Trinitro-9-fluorenylidene)-1,3-diethylthiobarbituric acid
5-(2,5-Dinitro-9-fluorenylidene)-1,3-diethylthiobarbituric acid
5-(2,6-Dinitro-9-fluorenylidene)-1,3-diethylthiobarbituric acid
5-(2,4,5,7-Tetranitro-9-fluorenylidene)-1,3-diethylthiobarbituric acid
5-(3,6-Dinitro-9-fluorenylidene)-1,3-diethylthiobarbituric acid
5-(2,4-Dicyano-9-fluorenylidene)-1,3-diethylthiobarbituric acid
5-(2,4,7-Tricyano-9-fluorenylidene)-1,3-diethylthiobarbituric acid
5-(2,4,5,7-Tetracyano-9-fluorenylidene)-1,3-diethylthiobarbituric acid
5-(2,4-Dichloro-9-fluorenylidene)-1,3-diethylthiobarbituric acid
5-(2,4,7-Trichloro-9-fluorenylidene)-1,3-diethylthiobarbituric acid
5-(2,4,5,7-Tetrachloro-9-fluorenylidene)-1,3-diethylthiobarbituric acid
5-(9-Fluorenylidene)-1,3-dimethylthiobarbituric acid
5-(2,4-Dinitro-9-fluorenylidene)-1,3-dimethylthiobarbituric acid
5-(2,4,7-Trinitro-9-fluorenylidene)-1,3-dimethylthiobarbituric acid
5-(2,5-Dinitro-9-fluorenylidene)-1,3-dimethylthiobarbituric acid
5-(2,6-Dinitro-9-fluorenylidene)-1,3-dimethylthiobarbituric acid
5-(2,4,5,7-Tetranitro-9-fluorenylidene)-1,3-dimethylthiobarbituric acid
5-(3,6-Dinitro-9-fluorenylidene)-1,3-dimethylthiobarbituric acid 5-(2,4-Dicyano-9-fluorenylidene)-1,3-dimethylthiobarbituric acid 5-(2,4,7-Tricyano-9-fluorenylidene)-1,3-dimethylthiobarbituric acid 5-(2,4-Dichloro-9-fluorenylidene)-1,3-dimethylthiobarbituric acid 5-(2,4,7-Trichloro-9-fluorenylidene)-1,3-dimethylthiobarbituric acid 5-(2,4,5,7-Tetrachloro-9-fluorenylidene)-1,3-dimethylthiobarbituric acid 5-(9-Fluorenylidene)-1,3-diphenylthiobarbituric acid 5-(2,4-Dinitro-9-fluorenylidene)-1,3-diphenylthiobarbituric acid 5-(2,4,7-Trinitro-9-fluorenylidene)-1,3-diphenylthiobarbituric acid 5-(2,6-Dinitro-9-fluorenylidene)-1,3-diphenylthiobarbituric acid 5-(2,4,5,7-Tetranitro-9-fluorenylidene)-1,3-diphenylthiobarbituric acid All of these thiobarbituric acid derivatives can be synthesized by dehydration-condensation of unsubstituted or substituted benzophenone or unsubstituted or substituted 9-fluorenone and 1,3-disubstituted thiobarbituric acid in the presence of an alkali as a catalyst, such as NaOH, KOH, CH$_3$COONH$_4$, ammonia and amine (e.g., diethylamine, triethylamine and piperidine), in accordance with the Knoevenagel condensation process as described in *Organic Reactions*, Vol. 15, pages 204 to 599 (1949).

Photoconductive polymers which can be used in this invention are those polymers containing a $\pi$ electron system in the main chain or in a side chain thereof.

Typical examples of such $\pi$ electron system include aromatic hydrocarbons such as naphthalene, anthrathene, pyrene, perillene, acenaphthene, phenylanthrathene, diphenylanthrathene, etc.; heterocyclic compounds such as carbazole, indole, acridine, 2-phenylindole, N-phenylcarbazole, etc.; and their derivatives substituted by halogen atom, lower alkyl group containing 1 to 6 carbon atoms or alkoxyl group containing 1 to 5 carbon atoms.

In this invention, those polymers containing these $\pi$ electron systems are used as photoconductive polymers. Examples of such polymers include vinyl polymers such as polyvinyl naphthalene, polyvinyl anthrathene, polyvinyl pyrene, polyvinyl perillene, polyacenaphthylene, polystyryl anthrathene, polyvinyl carbazole, polyvinyl indole, polyvinyl acridine, etc.; vinyl ether polymers such as polyanthorylmethylvinyl ether, polypyrenylmethylvinyl ether, polycarbazolylethylvinyl ether, polyindolylethylvinyl ether, etc.; epoxy resins such as polyglycidyl carbazole, polyglycidyl indole, poly-p-glycidyl anthorylbenzene, etc.; homo- or copolymers containing the $\pi$ electron system as a substituent, such as polybenzylacrylate, polybenzylmethacrylate, etc.; and condensation polymers of the above $\pi$ electron system compounds and formaldehyde. Of these polymers, poly-N-vinyl carbazole and N-vinyl carbazole copolymers are preferred.

Suitable N-vinyl carbazole copolymers are copolymers containing 50% by mol or more of the N-ethylene carbazole constitutional repeating unit of the formula

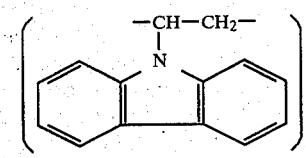

The constitutional repeating units making up the remainder of the N-vinyl carbazole copolymers which can be used include 1-phenylethylene, 1-cyanoethylene, 1-cyano-1-methylethylene, 1-chloroethylene, 1-(alkoxycarbonyl)-ethylenes, 1-(alkoxycarbonyl)-1-methylethylenes. These units are derived from styrene, acrylonitrile, methacrylonitrile, vinyl chloride, alkyl acrylates and alkyl methacrylates, respectively. As the alkyl group of the alkoxycarbonyl group, those alkyl groups containing 1 to 18 carbon atoms can be used, and suitable examples include a methyl group, an ethyl group, a hexyl group, a lauryl group, a stearyl group, and 4-methylcyclohexyl group. The term "constitutional repeating unit" as used herein is the same as defined in *Kobunshi*, Vol. 27, pages 345 to 359 (1978) (Japanese version of *Pure and Applied Chemistry*, Vol. 48, pages 373–385 (1976)).

With regard to the ratio of the thiobarbituric acid derivative of formula (1) or (2) to the photoconductive polymer which is used, the thiobarbituric acid derivative is employed in a ratio of 0.01 to 1.5 mols, preferably 0.4 to 1.2 mols, per mol of the constitutional repeating unit containing the $\pi$ electron system, present in the photoconductive polymer. Where the photoconductive polymer is poly-N-vinyl carbazole or an N-vinyl carbazole copolymer, the constitutional repeating unit containing the $\pi$ electron system is an N-ethylene carbazole unit.

Other known sensitizers, binders, plasticizers, dyes, pigments, etc., as necessary, can be incorporated as well as the above-described two components in the photoconductive composition of this invention within ranges not deteriorate characteristics of the photoconductive composition of this invention.

The photoconductive composition of this invention can be prepared by dissolving the above-described two essential components and other components employed as necessary in a suitable solvent in appropriate ratios to thereby provide a uniform solution (photoconductive composition solution) and then removing the solvent (for example, by evaporation). Depending upon the purpose, the photoconductive composition solution can be used as it is without removing the solvent.

The electrophotographic light-sensitive medium of this invention is prepared by coating the photoconductive composition solution as obtained above on a support with a surface of suitable electrical conductivity and then by drying the coating to form a photoconductive layer.

Depending upon the application where it is used, an adhesion layer may also be employed.

Solvents which are usually used in preparing the photoconductive composition solution are those solvents capable of dissolving both the photoconductive polymer and the bartituric acid derivative of the formula (1) or (2), such as tetrahydrofuran, dioxane, 1,2-dichloroethane, dichloromethane, monochlorobenzene, cyclohexanone, etc.

As supports with a conductive surface, drums or sheets of metals, e.g., aluminum copper, iron, zinc, etc., and paper, plastics, glass, etc., the surface of which is rendered electrically conductive by metal vapor-deposition, lamination of a metal foil, or by a method in which carbon black, a metal powder or the like is dispersed in a binder polymer and coated thereon, can be used as supports with an electrically conductive surface.

The photoconductive composition of this invention can be pulverized, dispersed in an electrically insulating solvent, and used in the electrophoresis photographic process as described in U.S. Pat. Nos. 3,384,565, 3,384,488 and 3,510,419 (corresponding to Japanese Patent Publication Nos. 21781/1968, 37125/1972 and 36079/1971, respectively) to form an image.

The photoconductive composition of the invention can be used for the preparation of a photoconductive layer of an image orthicon for a video camera, or for the preparation of a photoconductive layer of a solid image pickup tube element having a light-receiving layer (photoconductive layer) which is provided on the entire top surface of a two-dimensionally orientated semiconductor circuit for signal transmission or scanning.

The photoconductive composition of the invention is yellow or orange in color which results from the thiobarbituric acid derivatives represented by formula (1) or (2). Since these thiobarbituric acid derivatives constitute a charge transfer complex in combination with the constitutional repeating unit containing a $\pi$ electron system present in the photoconductive polymer, they have light-sensitivity in the regions of from ultraviolet light to visible light (from a wavelength of about 300 nm to a wavelength of about 760 nm).

The invention will be explained in greater detail with reference to the following examples.

EXAMPLES 1 TO 14

A mixture of 1 g of poly-N-vinyl carbazole (PVCz) and each of the thiobarbituric acid derivatives (ThBAD) shown in Table 1 (the amount of ThBAD added is shown as ThBAD/PVCz molar ratio in Table 1) was dissolved in 30 g of dichloroethane, and was coated on an electrically conductive layer (which had been prepared by providing a 60 nm thick $In_2O_3$ layer on a 100 μm colorless transparent polyethylene terephthalate film) so as to provide a coating film having a dry thickness of 1.5 μm. The coating film thus-formed was dried at 80° C. for 3 hours and was allowed to stand in a dark place overnight.

The coated film thus-processed could be charged to 200 V either positively or negatively. In either of the positive and negative chargings, the quantity of electrons held after 1 minute was 85% or more.

With both the positively charged and negatively charged coated films, 50% of the electrons charged was discharged on application of light in the amount indicated in Table 1. In all cases, a halogen lamp (illumination at the surface of the electrically conductive coated film: 40 lux to 4 lux) was used.

| Example No. | Thiobarbituric Acid Derivative | ThBAD/PVCz* Molar Ratio | Half-Reduction Exposure Amount (lux.sec) | |
|---|---|---|---|---|
| | | | Positive Charge | Negative Charge |
| 1 | (structure with two phenyl groups, C=C, thiobarbituric ring with Et, Et) | 0.1 | 650 | 870 |
| 2 | The same compound as No. 1 | 1 | 130 | 260 |
| 3 | (Cl-phenyl, phenyl, C=C, CO—N(Et), =S, CO—N(Et)) | 0.1 | 260 | 308 |
| 4 | The same compound as No. 3 | 1 | 85 | 115 |
| 5 | ($O_2N$-phenyl, phenyl, C=C, CO—N(Et), =S, CO—N(Et)) | 0.1 | 84 | 148 |
| 6 | The same compound as No. 5 | 1 | 60 | 120 |

-continued

| Example No. | Thiobarbituric Acid Derivative | ThBAD/PVCz* Molar Ratio | Half-Reduction Exposure Amount (lux.sec) | |
|---|---|---|---|---|
| | | | Positive Charge | Negative Charge |
| 7 | [structure: O₂N-phenyl, C=C, phenyl, CO-N(Me), =S, CO-N(Me)] | 1 | 78 | 135 |
| 8 | [structure: O₂N-phenyl, C=C, phenyl, CO-N(Ph), =S, CO-N(Ph)] | 1 | 50 | 110 |
| 9 | [fluorenylidene structure with CO-N(Et), =S, CO-N(Et)] | 0.1 | 210 | 400 |
| 10 | The same compound as No. 9 | 0.3 | 110 | 240 |
| 11 | [fluorenylidene structure with CO-N(Ph), =S, CO-N(Ph)] | 0.1 | 200 | 380 |
| 12 | [dinitrofluorenylidene structure with CO-N(Et), =S, CO-N(Et)] | 0.1 | 90 | 120 |
| 13 | [trinitrofluorenylidene structure with CO-N(Et), =S, CO-N(Et)] | 0.1 | 50 | 100 |
| 14 | The same compound as No. 13 | 1 | 9 | 15 |

*Mols of thiobarbituric acid derivative per mol of N-ethylenecarbazole constitutional repeating unit of PVCz.

EXAMPLE 15

A mixture of 0.2 g of poly-N-vinyl carbazole and 0.05 g of 5-(α-phenyl-p-nitrobenzylidene)-1,3-diethylthiobarbituric acid was dissolved in a mixed solvent of 100 g of methylene chloride and 50 g of an electrically insulative solvent, Isopar H (trade name for an isoparaffin-based petroleum solvent produced by Esso Petroleum Co.). Thereafter, on evaporation of the methylene chloride at 50° to 70° C., fine particles of poly-N-vinyl carbazole and 5-(α-phenyl-p-nitrobenzylidene)-1,3-diethylthiobarbituric acid which were mutually dissolved in each other were obtained in the state of a dispersion in the Isopar H.

Using the particle-dispersed solution thus-formed, the electrophoresis photographic process as described in Japanese Patent Publication No. 21781/1968 was followed wherein a minus voltage of 1,500 V was applied and light-exposure was applied for 2 seconds by use of a tungsten lamp in such a manner that the illumination at the surface of the particle-dispersed solution was 1 lux. Thus, an image was obtained.

What is claimed is:

1. A photoconductive composition comprising a mixture of a photoconductive substance and a thiobarbituric acid derivative represented by formula (1) or (2) below:

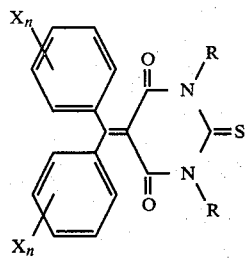

(1)

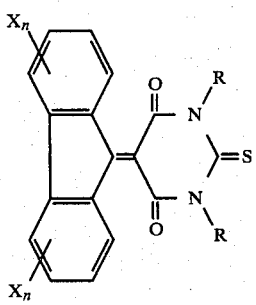

(2)

wherein X represents a hydrogen atom or a substituent having a Hammett's meta-position substituent constant ($\sigma m$) value of at least +0.2, n represents 1 or 2, and R represents an alkyl group containing 1 to 12 carbon atoms or a phenyl group.

2. The photoconductive composition as claimed in claim 1, wherein the photoconductive substance is a photoconductive polymer containing a $\pi$ electron system therein and the thiobarbituric acid derivative is present in said mixture in an amount of from 0.01 to 1.5 mols per mol of the constitutional repeating unit containing $\pi$ electron system present in the photoconductive polymer.

3. The photoconductive composition as claimed in claim 1 or 2, wherein said substituent having Hammett $\sigma m$ value of at least +0.2 is a cyano group, an acetyl group, a methoxycarbonyl group, an ethoxycarbonyl group, a carboxyl group, a nitro group, a —PO$_3$H group, a mercapto group, a methoxythiocarbonyl group, a methylsulfinyl group, a methylsulfonyl group, a sulfamoyl group, a fluorine atom, a chlorine atom, a bromine atom, an iodine atom, an iodyl group or a 2-nitrovinyl group, and said alkyl group for R is a methyl group, an ethyl group, a propyl group, a butyl group, a pentyl group, a hexyl group, a heptyl group, an octyl group, a nonyl group, a decyl group, a dodecyl group, an isopropyl group, an isobutyl group, an isoamyl group, an isohexyl group, a sec-butyl group, a neopentyl group, a tert-butyl group or a tert-pentyl group.

4. The photoconductive composition as claimed in claim 1 or 2, wherein X is a hydrogen atom, a chlorine atom, a bromine atom, a cyano group or a nitro group, and R is a methyl group, an ethyl group, a propyl group, a butyl group or an isopropyl group.

5. The photoconductive composition as claimed in claim 1 or 2, wherein said thiobarbituric acid derivative represented by formula (1) or (2) is 5-($\alpha$-phenyl-p-cyanobenzylidene)-1,3-dimethylthiobarbituric acid, 5-($\alpha$-phenyl-p-cyanobenzylidene)-1,3-diethylthiobarbituric acid, 5-($\alpha$-phenyl-p-cyanobenzylidene)-1,3-diphenylthiobarbituric acid, 5-($\alpha$-phenyl-p-nitrobenzylidene)-1,3-dimethylthiobarbituric acid, 5-($\alpha$-phenyl-p-nitrobenzylidene)-1,3-diethylthiobarbituric acid, 5-($\alpha$-phenyl-p-nitrobenzylidene)-1,3-diphenylthiobarbituric acid, 5-bis(p-chlorophenyl)methylene-1,3-diethylthiobarbituric acid, 5-bis(p-cyanophenyl)methylene-1,3-diethylthiobarbituric acid, 5-bis(p-nitrophenyl)methylene-1,3-diethylthiobarbituric acid, 5-(9-fluorenylidene)-1,3-diethylthiobarbituric acid, 5-(2,4-dinitro-9-fluorenylidene)-1,3-diethylthiobarbituric acid, 5-(2,4,7-trinitro-9-fluorenylidene)-1,3-diethylthiobarbituric acid, 5-(2,4-dicyano-9-fluorenylidene)-1,3-diethylthiobarbituric acid or 5-(2,4,7-tricyano-9-fluorenylidene)-1,3-diethylthiobarbituric acid.

6. The photoconductive composition as claimed in claim 1 or 2, wherein said photoconductive substance is a photoconductive polymer containing a $\pi$ electron system in the main chain or a side chain thereof, and the $\pi$ electron system is present in a moiety derived from an aromatic hydrocarbon selected from the group consisting of naphthalene, anthrathene, pyrene, perillene, acenaphthene, phenylanthrathene, and diphenylanthrathene or derived from a heterocyclic compound selected from the group consisting of carbazole, indole, acridine, 2-phenyl indole, N-phenylcarbazole, their halogen atom derivatives, and their lower alkyl group derivatives.

7. The photoconductive composition as claimed in claim 6, wherein said photoconductive polymer is a poly-N-vinyl carbazole or an N-vinyl carbazole copolymer.

8. An electrophotographic light-sensitive material comprising a support with an electrically conductive surface and a photoconductive composition layer provided thereon, said photoconductive composition comprising a mixture of a photoconductive substance and a thiobarbituric acid derivative represented by formula (1) or (2) below:

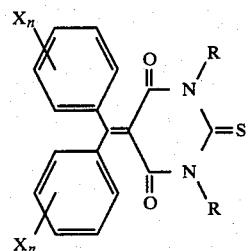

(1)

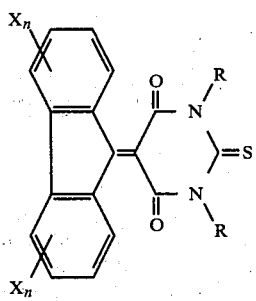

(2)

wherein X represents a hydrogen atom or a substituent having a Hammett's meta-position substituent constant ($\sigma m$) value of at least +0.2, n represents 1 or 2, and R represents an alkyl group containing 1 to 12 carbon atoms or a phenyl group.

9. The electrophotographic light-sensitive material as claimed in claim 8, wherein said photoconductive substance is a photoconductive polymer containing a π electron system therein, and the thiobarbituric acid derivative is present in said mixture in an amount of from 0.01 to 1.5 mols per mol of the constitutional repeating unit containing the π electron system present in the photoconductive polymer.

10. The electrophotographic light-sensitive material as claimed in claim 8, wherein said substituent having Hammett σm value of at least +0.2 is a cyano group, an acetyl group, a methoxycarbonyl group, an ethoxycarbonyl group, a carboxyl group, a nitro group, a —PO$_3$H group, a mercapto group, a methoxythiocarbonyl group, a methylsulfinyl group, a methylsulfonyl group, a sulfamoyl group, a fluorine atom, a chlorine atom, a bromine atom, an iodine atom, an iodyl group or a 2-nitrovinyl group, and said alkyl group for R is a methyl group, an ethyl group, a propyl group, a butyl group, a pentyl group, a hexyl group, a heptyl group, an octyl group, a nonyl group, a decyl group, a dodecyl group, an isopropyl group, an isobutyl group, an isoamyl group, an isohexyl group, a sec-butyl group, a neopentyl group, a tert-butyl group or a tert-phenyl group.

11. The electrophotographic light-sensitive material as claimed in claim 8, wherein X is a hydrogen atom, a chlorine atom, a bromine atom, a cyano group or a nitro group, and R is a methyl group, an ethyl group, a propyl group, a butyl group or an isopropyl group.

12. The electrophotographic light-sensitive material as claimed in claim 8, wherein said thiobarbituric acid derivative represented by formula (1) or (2) is 5-(α-phenyl-p-cyanobenzylidene)-1,3-dimethylthiobarbituric acid, 5-(α-phenyl-p-cyanobenzylidene)-1,3-diethylthiobarbituric acid, 5-(α-phenyl-p-cyanobenzylidene)-1,3-diphenylthiobarbituric acid, 5-(α-phenyl-p-nitrobenzylidene)-1,3-dimethylthiobarbituric acid, 5-(α-phenyl-p-nitrobenzylidene)-1,3-diethylthiobarbituric acid, 5-(α-phenyl-p-nitrobenzylidene)-1,3-diphenylthiobarbituric acid, 5-bis(p-chlorophenyl)methylene-1,3-diethylthiobarbituric acid, 5-bis(p-cyanophenyl)methylene-1,3-diethylthiobarbituric acid, 5-bis(p-nitrophenyl)methylene-1,3-diethylthiobarbituric acid, 5-(9-fluorenylidene)-1,3-diethylthiobarbituric acid, 5-(2,4-dinitro-9-fluorenylidene)-1,3-diethylthiobarbituric acid, 5-(2,4,7-trinitro-9-fluorenylidene)-1,3-diethylthiobarbituric acid, 5-(2,4-dicyano-9-fluorenylidene)-1,3-diethylthiobarbituric acid or 5-(2,4,7-tricyano-9-fluorenylidene)-1,3-diethylthiobarbituric acid.

13. The electrophotographic light-sensitive material as claimed in claim 8, wherein said photoconductive substance is a photoconductive polymer containing a π electron system in the main chain or a side chain thereof, and the π electron system is present in a moiety derived from an aromatic hydrocarbon selected from the group consisting of naphthalene, anthrathene, pyrene, perillene, acenaphthene, phenylanthrathene, and diphenylanthrathene or derived from a heterocyclic compound selected from the group consisting of carbazole, indole, acridine, 2-phenyl indole, N-phenylcarbazole, their halogen atom derivatives, and their lower alkyl group derivatives.

14. The electrophotographic light-sensitive material as claimed in claim 8, wherein said photoconductive substance is a poly-N-vinyl carbazole or an N-vinylcarbazole copolymer.

* * * * *